United States Patent
Kohler

(10) Patent No.: US 11,786,667 B2
(45) Date of Patent: Oct. 17, 2023

(54) LENTICULAR LABEL FOR A MEDICAL DEVICE

(71) Applicant: HOFFMANN-LA ROCHE INC., Little Falls, NJ (US)

(72) Inventor: Rémy Kohler, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 877 days.

(21) Appl. No.: 16/635,625

(22) PCT Filed: Aug. 10, 2018

(86) PCT No.: PCT/EP2018/071796
§ 371 (c)(1),
(2) Date: Jan. 31, 2020

(87) PCT Pub. No.: WO2019/030394
PCT Pub. Date: Feb. 14, 2019

(65) Prior Publication Data
US 2021/0132260 A1     May 6, 2021

(30) Foreign Application Priority Data
Aug. 11, 2017 (EP) .................................... 17185993

(51) Int. Cl.
*A61F 9/00*         (2006.01)
*G02B 3/00*        (2006.01)
(Continued)

(52) U.S. Cl.
CPC ....... *A61M 5/31525* (2013.01); *A61F 9/0026* (2013.01); *A61J 1/18* (2013.01); *A61M 5/20* (2013.01); *A61M 2205/583* (2013.01)

(58) Field of Classification Search
CPC ..... G02B 3/005; A61M 5/31525; A61M 5/20; A61F 9/0026; A61J 1/18; B42D 25/342
See application file for complete search history.

(56) References Cited

U.S. PATENT DOCUMENTS

| | | |
|---|---|---|
| 6,995,914 B1 | 2/2006 | Conley et al. |
| 8,236,209 B1 | 8/2012 | Conley |
| (Continued) | | |

FOREIGN PATENT DOCUMENTS

| | | |
|---|---|---|
| CN | 103080780 A | 5/2013 |
| CN | 104010676 A | 8/2014 |
| (Continued) | | |

OTHER PUBLICATIONS

Office Action issued in corresponding Chinese Patent Application No. 201880051842.6 dated Aug. 4, 2021.
(Continued)

*Primary Examiner* — Ryan D Howard
(74) *Attorney, Agent, or Firm* — MEDLER FERRO WOODHOUSE & MILLS PLLC

(57) ABSTRACT

A lenticular label for attachment to a surface of a medical device to be used in a pre-set orientation is disclosed. The lenticular label has a first face with a lens structure and a second face including a lenticular graphic resulting from a composition of a plurality of images. The images are aligned with the lens structure so that a different visual impression is obtained by changing a viewing angle from which the lenticular graphic is viewed with respect to the first face. The plurality of images includes a compliance image. The lens structure is arranged such that the compliance image is visible by a user when the lenticular label is attached to the medical device and the medical device is in the pre-set orientation. A medical device with such a lenticular label, and methods of use thereof are also disclosed.

12 Claims, 2 Drawing Sheets

(51) Int. Cl.
    *A61M 5/315*     (2006.01)
    *A61M 5/20*     (2006.01)
    *A61J 1/18*     (2023.01)

(56) References Cited

U.S. PATENT DOCUMENTS

2005/0152040 A1    7/2005  Goggins
2019/0061407 A1*  2/2019  Godfrey ............... B42D 25/425

FOREIGN PATENT DOCUMENTS

| | | |
|---|---|---|
| CN | 105683815 A | 6/2016 |
| CN | 106573102 A | 4/2017 |
| EP | 2 060 284 A1 | 5/2009 |
| WO | 99/07425 A1 | 2/1999 |
| WO | 2013128599 A1 | 9/2013 |
| WO | 2016/045699 A1 | 3/2016 |
| WO | 2016/193229 A1 | 12/2016 |

OTHER PUBLICATIONS

International Search Report dated Apr. 12, 2018 in corresponding International Application No. PCT/EP2018/071796.

* cited by examiner

LENTICULAR LABEL FOR A MEDICAL DEVICE

TECHNICAL FIELD

The present invention relates to a lenticular label for attachment to a surface of a medical device according to the preamble of independent claim 1 and more particularly to a lenticular label with a lens structure and a lenticular graphic into which a plurality of images is interlaced. The images and the lens structure are aligned in a way that a different visual impression is obtained by changing a viewing angle.

The present invention also relates to a medical device to be used in a pre-set orientation comprising a lenticular label as above introduced, as well as to a use of such a medical device.

BACKGROUND ART

Delivering a liquid or other fluid out of a container is required in many medical applications and performed in a plurality of different ways. Particularly where it is essential that the liquid is comparably precisely provided, specific devices are commonly used. For example, liquid pharmaceutical substances are often provided in glass or plastic vials which are closed by a septum or rubber plug and a cap clamped around it or another similar seal cover. Conventionally, for delivering the pharmaceutical substance out of vials, syringes can be used. Thereby, a needle of the syringe penetrates the septum or cover and the pharmaceutical substance is withdrawn into the syringe through its needle. Once transferred into the syringe, the pharmaceutical substance is delivered in an appropriate manner. For example, the pharmaceutical substance can be, e.g. subcutaneously or intramuscularly, injected or it can be orally applied or provided as droplets, e.g., in the eyes or nose of the patient.

Delivering liquids from vials or containers by means of syringes usually is comparably difficult. This typically makes it necessary that an educated person such as a doctor or a nurse is involved. In particular, in cases where the dosage of liquid delivered has to be comparably precise such as when comparable small volumes as in a range of ten microliter to about one milliliter are involved, patients are typically not capable of performing the delivery themselves when using a syringe or a similar device, i.e. self-administration can be challenging for the user. However, self-administration of liquids or medicaments is beneficial in many therapeutic applications since the effort for the patient and the costs of the therapy can be extensively reduced.

For improving this situation, there are devices used which allow for more conveniently delivering a comparably precise volume of liquids. For example, it is known to provide medicaments in prefilled syringes which can be administered by the patients themselves. Manual injection by a syringe, though, requires specific skills which need to be developed through a learning process and normally are owned by professional operators such as nurses. Many patients remain apprehensive about injecting themselves using substantially regular syringes.

Therefore, automatic medicament delivery devices have been developed, such as auto-injector devices, which help to improve patient self-reliance and medicine adherence by making injections simpler and more manageable.

However, existing automatic delivery devices still require some handling skills and a correct manipulation by a user can be paramount both, e.g., when dosing such as transferring a predefined amount of medicament from a vial into a dedicated dosage chamber of the delivery device, and when delivering such as injecting the dosed amount of medicament.

In fact, the correct use of known (semi-)automatic delivery devices involves an assessment of parameters, which are difficult to estimate by a relatively untrained user, such as a patient. For example, for an accurate dosing the respective mechanisms of known delivery devices require that the device is in a correct orientation. Particularly, when dosing comparably small amounts, an inappropriate orientation of the medical device can affect the dosing. For example, dosing mechanisms may require that the medicament to is adjacent to the cap of the vial while being dosed. In such embodiments, turning the delivery device upside down could cause the dosing not to work at all. Also during delivery, the orientation of the delivery device can be important.

Therefore, there is a need for a medical device or an auxiliary for such a device which may provide an effective guidance for users who need to self-administer a predetermined dose of medicament, such that the users can easily and with confidence comply with the requirement that the medical device be correctly manipulated and oriented for an appropriate dosing and administration.

DISCLOSURE OF THE INVENTION

According to the invention this need is settled by a lenticular label as it is defined by the features of independent claim 1, and by a medical device as it is defined by the features of independent claim 7. Preferred embodiments are subject of the dependent claims.

In particular, the invention deals with lenticular label for attachment to a surface of a medical device, such as for instance a medical delivery device for (self-)administration of a medicament, which is meant to be used in a pre-set orientation for a correct employment. In the context of the present invention, by the term "attachment" any kind of affixing the lenticular label to the medical device is meant, either to an external surface thereof or to an internal surface thereof. The attachment is preferably such as to make the lenticular label integral with the medical device, in a way that a movement of the medical device corresponds to a proportional movement of the lenticular label. The term "medical device" can relate to any device used in a medical application, wherein its orientation is of importance in any step of application. As mentioned, the medical device can particularly be a medical delivery device such as an auto-injector or the like.

The lenticular label has a first face, for instance a front face, with a lens structure. The lens structure can take the form of an array or series of thin lenses which may be, for instance, molded on the label and extend over a lenticulated region.

The lenticular label also has a second face, for instance on the back side of the label, including a lenticular graphic. The lenticular graphic results from a composition of a plurality of images such as by the plurality of images being interlaced to the lenticular graphic. The lenticular graphic therefore preferably comprises interleaved line or other geometric elements from the multiplicity of images composing the lenticular graphic. The first and the second faces are preferably, but not necessarily, substantially parallel.

The lenticular graphic is aligned in relation to the lens structure so that a different one of the plurality of images is visible by changing a viewing angle from which the lenticular graphic is viewed with respect to the first face. In other words, different visual impression, which substantially corresponds to each of the plurality of images, become successively visible depending on the given or current viewing angle.

The viewing angle can be defined by an angle between a direction of vision of a user or patient and the first face of the lenticular label. Thereby, the term "direction of vision" can relate to a direction, plane or axis in which the eyes of the user or patient are oriented or focused when looking at the lenticular label. The viewing angle preferably correlates to the holding angle at which the medical device to which the lenticular label is attached is held by a user.

The plurality of images comprises a compliance image. The lens structure is arranged such that the compliance image is visible by a user of the medical device when the lenticular label is attached to the medical device and the medical device is in the pre-set orientation.

The term "pre-set orientation" relates to a predefined orientation the medical device is to align in order that a proper and accurate functioning can be achieved. The pre-set orientation can be substantially the orientation which guarantees a correct use of the medical device, for instance in terms of a correct execution of a medicament dosing from a vial into a dosing chamber of the medical device and/or of a correct execution of a medicament delivery.

Thanks to the special arrangement of the lens structure, based on a dimension of the viewing angle, the lenticular label according to the present invention is designed to visually signal to a user, who is handling and looking at the medical device to which the lenticular label is attached, whether the medical device is held in the pre-set orientation. This may guarantee a correct use or an accurate dosing of the medical device. Also, it can indicate that the medical device should rather be moved to reach the pre-set orientation.

Thereby, such instantaneous visual guidance to a user of the medical device can be of immediate interpretation and actually provide a clear indication that the medical device is ready for use by showing the compliance image. Or, it allows a prompt adjustment to obtain the pre-set orientation by simply showing an image other than the compliance image on the lenticular label.

Preferably, the representation of the compliance image schematically and intuitively conveys the message that the medical device, integral with the lenticular label of the present invention, is in the pre-set orientation suitable to correctly carry out the desired medical device functions. For example, the compliance image can comprise an acronym like "OK", a thumb up sign or the like.

Preferably, at least one of the plurality of images, other than the compliance image, shows a direction of adjustment to bring the medical device in the pre-set orientation. This may preferably the case, for instance, if the viewing angle is larger than a given threshold angle.

Further to that, preferably at least one of the plurality of images, other than the compliance image, shows an indication of the extent to which the viewing angle needs to be adjusted in order to bring the medical device to the pre-set orientation. If the viewing angle is larger than a given threshold angle, this may result in an indication which signals to decrease the viewing angle.

For a more continuous guidance in achieving a correct positioning of the medical device to which the lenticular label according to the present invention is associated, the plurality of images preferably show a sequence of adjustment steps of the viewing angle in order to bring the medical device to the pre-set orientation. Each of these steps may represent an intermediate status in the process of adjustment, wherein for each adjustment step of the sequence, an indication may be shown of the extent to which the viewing angle needs to be adjusted in order to bring the medical device to the pre-set configuration.

The sequence of adjustment steps portrayed on the lenticular label and showing at respective viewing angles can, for instance, comprise from four to ten such as seven different images corresponding to respective orientations of the medical device.

The compliance image may remain the same for a range of admissible viewing angles which guarantee that the medical device is in the pre-set configuration suitable for carrying out the desired operations.

Preferably, when the viewing angle is larger than a given threshold angle, the lenticular label is configured to show to the user of the medical device one of the plurality of images other than the compliance image, the image shown corresponding to the current orientation of the medical device. When, instead, the viewing angle is equal to, or smaller than, the given threshold angle, the lenticular label is preferably configured to show to the user of the medical device the compliance image.

The lenticular label may be configured so that the given threshold angle is comprised in a range of [90°+δ, 90°, 90°−δ]. In this case, for a viewing angle formed between a viewing direction, or axis, of a medical device user and the first face of the lenticular lens attached to the medical device which is comprised in a range of [90°+δ, 90°, 90°−δ], the lenticular lens shows the compliance image.

The present invention also relates to a medical device to be used in a pre-set orientation, comprising a lenticular label as above described. The lenticular label integrated with the medical device has a first face with a lens structure and a second face including a lenticular graphic resulting from a composition of a plurality of images.

The lenticular graphic is aligned with the lens structure so that a different on the plurality of images is visible or a different visual impression is obtained by changing a viewing angle from which the lenticular graphic is viewed with respect to the first face.

The plurality of images comprises a compliance image. The lens structure is arranged such that, when the medical device is in the pre-set orientation, the compliance image is visible by a user of the medical device, and otherwise an image other than the compliance image is visible.

Preferably, the lenticular label is integral with the medical device or attached or affixed to an external or an internal surface of the medical device. The lenticular label may be made integral with the medical device by adhesive and/or mechanical fastening means and/or by some embedment process firmly fixing the lenticular label into a material of the medical device component. In the latter case, the lenticular label may be visibly embedded into a component of the medical device, wherein the component preferably has a face of substantially transparent material through which the lenticular label shows.

The medical device according to the present invention may be a dosing and/or an injection device. In this case, the lenticular label is preferably configured to signal whether the medical device is in a correct dosing orientation or not. The lenticular label may also, or alternatively, be designed to signal whether the medical device is in a correct delivery position, for instance suitable for injection of a medicament.

For these purposes, the lenticular label is preferably made integral to a surface of a dosing activator component or to a surface of an injection component of the medical device engaged to the dosing activator component or to an assembly of the dosing activator component and the injection component.

At any rate, the position and arrangement of the lenticular label according to the present invention are preferably such that the visual impression obtained in a given viewing angle reflects, substantially instantly, the current orientation of the medical device with which it is integral. As mentioned, in the context of the present invention, the viewing angle is the angle from which the lenticular graphic is viewed by a user with respect to its first face. For a given viewing position of a user looking at the medical device according to a given viewing axis, the orientation of the medical device substantially corresponds to the angle at which a user holds the medical device and is preferably univocally defined by the above viewing angle.

The present invention also relates to the use of a lenticular label as above described, for visually indicating, or signalling, to a user an orientation of a medical device with which the lenticular label is made integral. In particular, the lenticular label described can be advantageously employed to visually render representations corresponding to the current orientation of a medical device with which the lenticular label is made integral.

Such representations constitute, therefore, a valid guide for a user to establish whether the medical device handled is actually positioned according to a pre-set orientation, necessary for carrying out a procedure appropriately, or, rather, should be moved to it for a safe procedure. Specifically, a conformity image is shown by the lenticular lens when the medical device is in a pre-set orientation.

BRIEF DESCRIPTION OF THE DRAWINGS

The lenticular label according to the invention and the medical device comprising such lenticular label according to the invention are described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figures 1L, 1S:
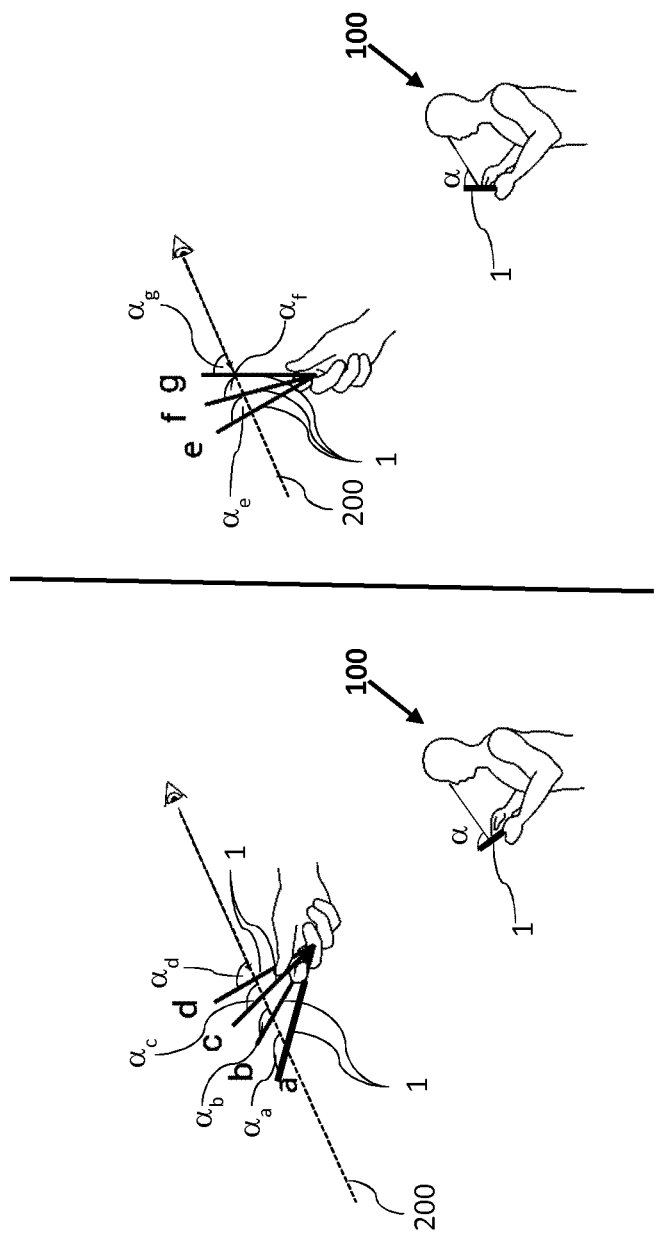
FIGS. 1*l* and 1*s* schematically show a user holding, in seven different orientations, a medical device to which a lenticular label according to the present invention is attached.

Referring to the embodiment of FIGS. 1*l* and 1*s*, a mode of use of a medical device 1 according to the present invention integrating a lenticular label 2 according to the present invention is schematically shown. A user 100 holds, in overall seven different orientations, the medical device 1 to which the lenticular label 2 according to the present invention is attached. More specifically, it is represented how—for a given viewing position taken by a user 100 of a medical device 1 who looks at the medical device 1 according to a given viewing axis 200—the holding angle at which the medical device 1 is held correlates to a viewing angle α from which a lenticular graphic of the lenticular label 2 is viewed with respect to a first face of the label.

In FIG. 1*l*, four distinct positions a, b, c, d are shown at which the medical device 1 is held by the user 100. For each of the positions a, b, c and d, the user holds the medical device 1 at different holding angles, that is the medical device is differently oriented. Such holding angles of the medical device 1, or, otherwise said, such orientations of the medical device 1, are correlated to respective four viewing angles αa, αb, αc, αd formed between the viewing axis 200 and the first face of the lenticular label 2 integrated in the medical device 1. The first face of the lenticular label 2 (i.e. in the present case, the front face, oriented towards the eyes of the user 100) is provided with a lens structure.

Thus, the orientations of the medical device 1 substantially correspond to the angles at which a user holds the medical device 1 and are, in FIG. 1*l*, univocally defined by the above viewing angles αa, αb, αc, αd.

The medical device 1 is meant to be used in a pre-set orientation which guarantees a correct use thereof, for instance in terms of a correct execution of a medicament dosage in a dosing chamber of the medical device 1 and/or of a correct execution of a medicament delivery.

In FIG. 1*s*, three further distinct positions e, f, and g are shown at which the medical device 1 is held by the user 100. For each of the positions e, f, and g, the user holds the medical device 1 at different holding angles, that is the medical device is differently oriented, similarly to what already explained for FIG. 1*l*, mutatis mutandis. Thus, the orientations of the medical device 1 in FIG. 1*s* are univocally defined by the viewing angles αe, αf and αg.

The first face of the lenticular label 2 is provided with a lens structure.

A second face of the lenticular label 2 (for instance, the back face, oriented opposite to the eyes of the user 100) includes a lenticular graphic into which a plurality of images is interlaced, that is the lenticular graphic results from a composition of such a plurality of images. The images on the second face are aligned with the lens structure on the first face so that a different visual impression is obtained by changing the viewing angle α from which the lenticular graphic is viewed with respect to the first face.

The viewing angles αa, αb, αc, αd, αe, αf and αg substantially correspond to the angles from which the lenticular graphic is viewed, with respect to the first face.

Figure 2:
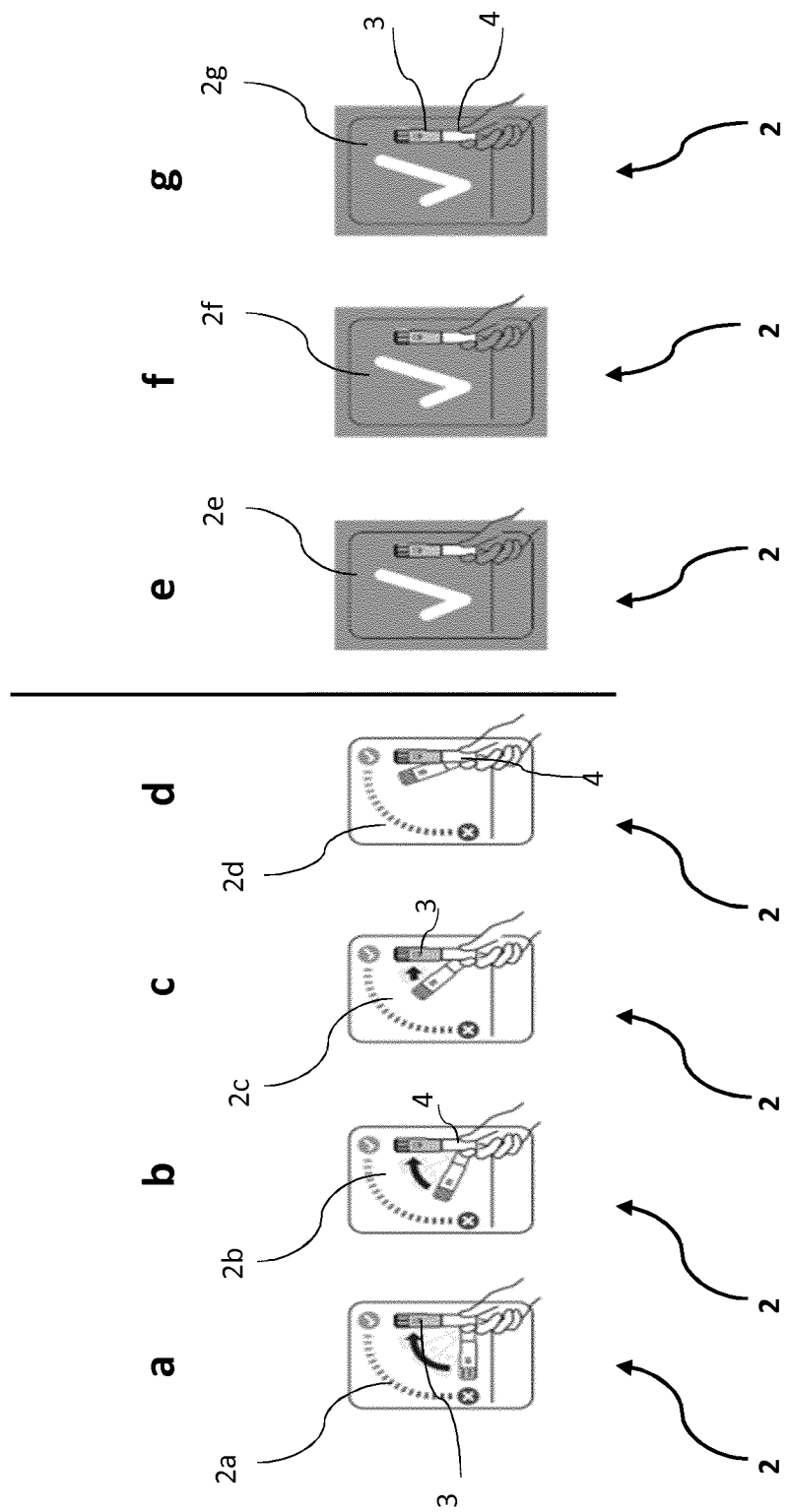
FIG. 2 schematically shows a sequence of visual impressions, or images, showing on the lenticular label of FIGS. 1*l* and 1*s*, in correlation with each of the seven different orientations taken by the medical device.

FIG. 2 shows a sequence of seven images 2a, 2b, 2c, 2d, 2e, 2f, 2g which can be interlaced into the lenticular graphic of the lenticular label 2, in a way that the visual impression offered to a viewer, or to a medical device user 100, by each one of them respectively, immediately conveys the current medical device orientation in correspondence with viewing angles αa, αb, αc, αd, αe, αf and αg.

In each of the images of FIG. 2, it is also shown a correlation between the current medical device orientation and the pre-set orientation suitable to correctly carry out the desired medical device functions.

Images 2a, 2b, 2c, 2d of the lenticular label 2 from positions a to d show a direction of adjustment to bring the medical device 1 in the pre-set orientation. In the viewing angle is larger than a given threshold angle, as it is the case for viewing angles αa, αb, αc, αd, the respective images 2a, 2b, 2c, 2d represent a non-compliance situation wherein the medical device is not in the pre-set orientation suitable to correctly carry out the desired medical device functions. The misalignment from the compliance situation is displayed as progressively reduced from the representation of image 2a to the representation of image 2d, as a user 100 is guided to bring the medical device 1 in the pre-set orientation. As a further guidance, images of the lenticular label 2 from 2a to 2d also show an indication of the extent to which the viewing angle αa, αb, αc, αd needs to be adjusted in order to bring the medical device 1 to the pre-set orientation. In the present case, an indication in the form of an arrow signals to decrease the viewing angle, which entails for the user 100 to modify the grip and the holding position of the medical device 1. Each of images from 2a to 2d represents an intermediate status in the process of adjustment.

Images 2e, 2f and 2g of the lenticular label 2 show the same compliance image which schematically and intuitively conveys the message that the medical device 1 is in the pre-set orientation suitable to correctly carry out the desired medical device functions. The compliance image represented in images 2e, 2f and 2g comprises a sign of confirmation, in the form of a tick mark symbol, that the medical device 1 is in the pre-set orientation, plus a representation of the medical device 1 in a substantially upright position which is assumed, in this case, as representative of the pre-set orientation.

In this case, the compliance image remains the same for a range of admissible viewing angles αe, αf, αg which guarantee that the medical device 1 is in the pre-set configuration suitable for carrying out the desired operations. The viewing angles αe, αf and αg are either equal to, or smaller than, a given threshold angle: in such situation, the lenticular label 2 is configured to show to the user 100 of the medical device 1 the compliance image.

The lenticular label 2 is configured so that the given threshold angle is comprised in a range of about 130° to about 90°, wherein the threshold angle preferably is about 130°, about 120°, about 110°, about 100° or about 90°.

With reference to the simplified representation of a medical device 1 in the images of FIG. 2, the lenticular label 2 can be made integral to a surface of a dosing activator component 3 or to a surface of an injection component 4 of the medical device 1, engaged to the dosing activator component 3, or to an assembly of the dosing activator component 3 and the injection component 4.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A lenticular label for attachment to a surface of a medical device to be used in a pre-set orientation, the lenticular label comprising:
   a first face with a lens structure; and
   a second face including a lenticular graphic resulting from a composition of a plurality of images, the lenticular graphic being aligned with the lens structure so that a different one of the plurality of images is visible by changing a viewing angle from which the lenticular graphic is viewed with respect to the first face, wherein the plurality of images comprises a compliance image, and wherein the lens structure is arranged such that the compliance image is visible by a user of the medical device when the lenticular label is attached to the medical device and the medical device is in the pre-set orientation.

2. The lenticular label of claim 1, wherein at least one image of the plurality of images, other than the compliance image, shows a direction of adjustment to bring the medical device in the pre-set orientation.

3. The lenticular label of claim 1, wherein at least one image of the plurality of images, other than the compliance image, shows an indication of the extent to which the viewing angle needs to be adjusted in order to bring the medical device to the pre-set orientation.

4. The lenticular label of claim 3, wherein images of the plurality of images show a sequence of adjustment steps in order to bring the medical device to the pre-set orientation.

5. The lenticular label of claim 1, wherein when the viewing angle is larger than a given threshold angle, the lenticular label is configured to show to the user of the medical device at least one image of the plurality of images other than the compliance image, and when the viewing angle is equal to, or smaller than, the given threshold angle, the lenticular label is configured to show the compliance image to the user of the medical device.

6. The lenticular label of claim 5, wherein the given threshold angle is in a range of about 130° to about 90°, or wherein the given threshold angle is about 130°, about 120°, about 110°, about 100° or about 90°.

7. A method of use of the lenticular label according to claim 1 for visually indicating, or signaling, to a user an orientation of a medical device with which the lenticular label is made integral.

8. A medical device to be used in a pre-set orientation, comprising:

a lenticular label having a first face with a lens structure and a second face including a lenticular graphic resulting from a composition of a plurality of images, the plurality of images being aligned with the lens structure so that a different one of the plurality of images is visible by changing a viewing angle from which the lenticular graphic is viewed with respect to the first face, wherein, the plurality of images comprises a compliance image, and the lens structure is arranged such that when the medical device is in the pre-set orientation, the compliance image is visible by a user of the medical device, and otherwise, an image other than the compliance image is visible.

9. The medical device of claim 8, wherein the lenticular label is integral with the medical device or affixed to an external surface or to an internal surface of the medical device.

10. The medical device of claim 8, wherein the lenticular label is visibly embedded into a component of the medical device.

11. The medical device of claim 8, wherein the medical device is a dosing and/or an injection device and the lenticular label is configured to signal whether the medical device is in a correct dosing orientation or not.

12. The medical device of claim 11, wherein the lenticular label is made integral with a surface of a dosing activator component, with a surface of an injection component of the medical device engageable to the dosing activator component, or with an assembly of the dosing activator component and the injection component.

* * * * *